(12) United States Patent
Chermann et al.

(10) Patent No.: US 7,306,798 B2
(45) Date of Patent: Dec. 11, 2007

(54) IMMUNOGLOBULIN IGG3 AS A MARKER FOR PROTECTING AGAINST INFECTIOUS VIRAL DISEASES, AND THE USES OF THE SAME

(75) Inventors: Jean-Claude Chermann, Cassis (FR); Camille Haslin, Marseilles (FR); Ricardo De Oliveira, Sao Paulo (BR)

(73) Assignees: Urrma R & D (FR); Urrma Biopharma (CA)

( * ) Notice: Subject to any disclaimer, the term of this patent is extended or adjusted under 35 U.S.C. 154(b) by 0 days.

(21) Appl. No.: 10/504,802

(22) PCT Filed: Feb. 13, 2003

(86) PCT No.: PCT/FR03/00463

§ 371 (c)(1),
(2), (4) Date: Aug. 13, 2004

(87) PCT Pub. No.: WO03/068820

PCT Pub. Date: Aug. 21, 2003

(65) Prior Publication Data

US 2005/0152910 A1    Jul. 14, 2005

(30) Foreign Application Priority Data

Feb. 15, 2002    (FR) .................................. 02 01960

(51) Int. Cl.
*A61K 39/395* (2006.01)
*A61K 39/00* (2006.01)
*A61K 39/42* (2006.01)

(52) U.S. Cl. ............................. 424/130.1; 424/139.1; 424/141.1; 424/147.1; 424/148.1

(58) Field of Classification Search .............. 424/139.1
See application file for complete search history.

(56) References Cited

U.S. PATENT DOCUMENTS

| 5,348,876 A | 9/1994 | Michaelsen et al. |
| 6,113,902 A | 9/2000 | Chermann et al. |
| 2003/0021800 A1 | 1/2003 | Chermann et al. |

FOREIGN PATENT DOCUMENTS

EP    0 470 989 B1    7/1994

OTHER PUBLICATIONS

Wei, X. Antibody neutralization and escape by HIV-1. Nature vol. 422 (Mar. 20, 2003), pp. 307-312.*
Buckley, R. IgG Subclass Deficiency (Dec. 1998). Clinical Focus on Primary Immune Deficiencies vol. 1(3) [online], [retrieved on Dec. 22, 2005]. Retrieved from the internet <URL: www.primaryimmune.org/pubs/clinic_focus/cf_dec98.pdf>.*
Hassan, M.S. Biological half-life of normal and truncated human IgG3 in scid mice. European Journal of Immunology vol. 21(5) (May 1991), pp. 1319-1322.*
Galea et al., "Identification of a biological marker of resistance to AIDS progression", Cellular Pharmacology AIDS Science, vol. 3, pp. 311-316, 1996.
Scharf et al., "Immunoglobulin G3 from Polyclonal Human Immunodeficiency Virus (HIV) Immune Globulin Is More Protent than Other Subclasses in Neutralizing HIV Type 1", Journal of Virology, pp. 6558-6565, Jul. 2001.
Kunert et al., "Stable Recombinant Expression of the Anti HIV-1 Monoclonal Antibody 2F5 After IgG3/IgG1 Subclass Switch in CHO Cells", Biotechnology and Bioengineering, vol. 67, No. 1, pp. 97-103, Jan. 5, 2000.
Raux et al., "IgG Subclass Distribution in Serum and Various Mucosal Fluids of HIV Type 1—Infected Subjects", Aids Research and Human Retroviruses, vol. 16, No. 6, pp. 583-594, Nov. 6, 2000.
Haslin et al., "Anti-R7V antibodies as therapeutics for HIV-infected patients in failure of HAART", Pharmaceutical Biotechnology, vol. 13, pp. 621-624, 2002.
Rubinstein et al., "Preliminary Results of V3 Loop Peptide-Primary Neutralizing Domain Conjugate Phase 1 Vaccine Trial", Aids Research and Human Retroviruses, vol. 10, Supp. 2, pp. S149-S153, 1994.
Cavacini et al., "Influence of heavy chain constant regions on antigen binding and HIV-1 neutralization by a human monoclonal antibody", Journal Of Immunology, vol. 155, No. 7, p. 3638, 1995.
P. Galea, C. Le Contel, J.C. Chermann, "A Novel Epitope R7V Common To All HIV-1 Isolates Is Recognized By Neutralizing IgG Found In HIV-Infected Patients And Immunized Rabbits", Vaccine 17 (1999) 1454-1461.

* cited by examiner

*Primary Examiner*—Jeffrey S. Parkin
*Assistant Examiner*—Louise Humphrey
(74) *Attorney, Agent, or Firm*—Lerner, David, Littenberg, Krumholz & Mentlik, LLP (57) ABSTRACT

The invention relates to a novel variant of isolated and/or purified immunoglobulin IgG3 which can be used as a marker for protecting against infectious viral diseases such as AIDS, as a diagnostic tool, or as a preventive and curative medicament. The invention also relates to corresponding in vitro diagnostic methods.

6 Claims, 6 Drawing Sheets

Immunoprecipitation of different strains of virus with 10 μg of ARG CH IgG3 or 40 μg of ETC MA IgG3

Legend: ARG CH, ETC MA, Seronegative control, Virus control

Strains:
- UG 92029 (07/07/98) A: 43.4, 33.8, 1.4
- BRU (07/13/00) B: 74.1, 35, 3.6
- BR 92025 (18/10/00) C: 27.8, 10.7, 1.1
- NDK (29/02/96) D: 79, 29.3, 0.7
- THA 92022 (29/05/98) E: 9.4, 19, 1.1
- BR 93029 (18/10/00) F: 56.2, 31.5, 0.9
- YBF 30 (22/01/99): 46.8, 29.2, 2

Y-axis: Precipitation percentage (0–90)

FIGURE 6

SEQUENCE LISTING

<160> NUMBER OF SEQ ID NOS: 1

<210> SEQ ID NO 1
<211> LENGTH: 7
<212> TYPE: PRT
<213> ORGANISM: Human immunodeficiency virus type 1

<400> SEQUENCE: 1

Arg Thr Pro Lys Ile Gln Val
1               5

IMMUNOGLOBULIN IGG3 AS A MARKER FOR PROTECTING AGAINST INFECTIOUS VIRAL DISEASES, AND THE USES OF THE SAME

CROSS-REFERENCE TO RELATED APPLICATIONS

This application is a national phase entry under 35 U.S.C. § 371 of International Application No. PCT/FR03/00463 filed Feb. 13, 2003, which claims priority from French application 0201960, filed Feb. 25, 2002.

FIELD OF THE INVENTION

The present invention relates to the field of biology and more particularly concerns a new variant of isolated and/or purified immunoglobulin IgG3, useful as a protective marker for infectious viral diseases such as AIDS, and as a diagnostic tool or as a preventative and curative medicament.

BACKGROUND OF THE INVENTION

AIDS is an extremely serious and worrying public health problem for many countries throughout the world. In the USA, for example, the official number of AIDS cases is greater than 100,000 and the number of people infected has been estimated at more than 1 million. The propagation of the disease is accentuated by the number of chronic bearers of the virus responsible for AIDS who remain asymptomatic for many years, or even their entire life, and are therefore unidentified sources of infection. This disease, which can be transmitted by sexual contact and via the blood, affects the immune system of the host, thus causing the appearance of opportunistic infections or of pathologies against which the host would have been protected by a healthy immune system. Once AIDS has been recognized, death usually occurs two to three years after diagnosis following a breakdown of the patient's immune defences and multiple opportunistic infections. It is very difficult to classify the AIDS viruses given the extreme genetic and antigenic variability they exhibit; conventionally, it is acknowledged that there are two types of virus responsible for human AIDS: HIV-1 and HIV-2 (human immunodeficiency virus). For a number of reasons, the HIV replication mechanism poses many problems in terms of obtaining effective treatment. This is because proviral DNA, on account of its integration in the cell genome, behaves likes a genetic element of the host. Moreover, the HIV virus is disseminated throughout the entire body in the T lymphocytes, the monocytes, the macrophages and in the central nervous system. Finally, the HIV virus has extremely high antigenic variability. The various curative therapies currently used in clinical medicine consist essentially either in blocking the activity of reverse transcriptase or in inhibiting the activity of viral enzymes that are indispensable for infection or replication (proteases, integrases). The effectiveness of these therapies remains limited since the absorption of these antivirals causes side effects. Moreover, given the high rate of mutation of the HIV virus, the latter rapidly becomes resistant to drugs, such as AZT and other nucleotide analogues, during therapy. The emergence of resistant strains makes it necessary to increase the therapeutic doses administered to patients. Failure of current curative therapies therefore means that it is necessary to develop new therapeutic strategies for fighting retroviral infection.

In their research to develop new curative strategies, the inventors have been led to study the HIV-positive populations who are infected with HIV but are non-progressors, that is to say have not developed AIDS. They have thus been able to show for the first time that in these HIV-positive patients who are infected with HIV classified as non-progressors there is a particular variant of IgG3. The inventors have shown that this variant of IgG3 differs by its primary structure of lower molecular weight, its longer half-life and its higher serum concentration than in the case of conventional IgG3s. The immunoglobulin IgG3 demonstrated by the inventors, which has been isolated and purified, appears to be a protective marker for AIDS and an agent which neutralizes the causative agent of this disease.

Human immunoglobulin IgGs can be divided into four subclasses (IgG1, IgG2, IgG3, IgG4) which differ by minor differences in the primary structure of their heavy chain. The main differences concern the hinge region and the number of inter-chain disulphide bridges. Thus, the hinge region of IgG3 is very long, which accounts for its higher molecular weight (170 kDa) and certain biological properties such as its half-life (in days) which is much shorter for immunoglobulin IgG3s (7 days) than for the other IgG subclasses which have a half-life of around 20 days. IgG3s are capable of selectively binding to certain receptors to the Fc fragment of immunoglobulins such as RFcγI, RFcγIIa, RFcγIIIa. Immunoglobulins, the primary function of which is to bind the antigen so as to neutralize it, also have the role of activating secondary effector functions in particular by way of the complement. The complement system, which is a complex group of serum proteins involved in inflammatory reactions, is one of the most important effector mechanisms for human IgG1s, IgG3s and IgGMs. After having bound the antigen, the IgG1s, IgG3s and IgGMs can activate the enzymatic cascade in the conventional manner of the complement known as C1q, IgG2s for their part being relatively ineffective and IgG4s being incapable of doing so. The binding of C1q to the immunoglobulin is the first step in the cascade of the complement which leads to cell lysis. This mechanism is particularly important for fighting infectious and viral diseases such as AIDS, for example, and plays a crucial role in destroying infected cells.

SUMMARY OF THE INVENTION

The work carried out by the inventors thus makes it possible to meet an urgent need, namely the need to develop new preventive and/or curative medicaments or compositions intended to neutralize the AIDS virus, and also to develop new diagnostic tests which make it possible to adapt the therapy as a function of the serotype of the patient.

The subject of the present invention is therefore a purified and/or isolated human immunoglobulin of class IgG3, or one of the fragments thereof, having the following characteristics (i) a life span in the serum of the patient which is greater than the life span of the IgG3s normally present in human serum and in particular of at least 15 days, preferably of at least one month, (ii) a heavy chain, the molecular weight of which, determined by electrophoretic mobility, is less than the molecular weight of the IgG3s normally present in human serum (60 kDa), said heavy chain having a molecular weight of about 50 kDa and comprising the complement binding site. This reduction in the apparent molecular weight determined by electrophoresis reflects either a reduction in length of the primary structure of the IgG3 or a different three-dimensional shape or a reduction in the number of post-translational modifications such as, for example, the glycosylation of the heavy chain.

The variant immunoglobulin IgG3 according to the invention in serum is finally characterized by a serum concentration that is at least once as great, at least twice as great, in general at least three times as great as the IgG3 concentration of a normal serum, which represents a serum concentration of this new IgG3 variant of about 1 g/L.

According to one embodiment of the invention, the variant immunoglobulin IgG3 is isolated and/or purified from HIV-positive patients; these patients are non-progressors, that is to say people who have been infected with HIV for a number of years without any loss of immune defence, and who are thus asymptomatic. More preferably, the immunoglobulin IgG3 according to the invention selectively binds the R7V epitope of the gp160 protein of the HIV-1 virus, said epitope comprising the sequence Arg-Thr-Pro-Lys-Ile-Gln-Val. (SEQ ID NO: 1)

BRIEF DESCRIPTION OF THE DRAWINGS

FIGS. 1A-1E are photographs of electrophoretic gels; FIG. 1A shows a comparison of an $IgG_3$ of a normal serum (SN1) with that of a non-progressor HIV-positive patient (ARG); FIG. 1B shows a confirmation of the lower molecular weight of the heavy chain with another patient (ETC); FIG. 1C shows other patients (THO, GEM); FIG. 1D shows other patient (VAL) and other HIV-negative person (SN2); and FIG. 1E shows other patient (BOI)

DETAILED DESCRIPTION

In the present description, the terms immunoglobulin and antibody will be used without distinction. The term epitope is intended to mean any determinant of the protein responsible for specific interaction with the antibody; epitopes usually consist of groups of molecules having chemically active surfaces such as amino acids or side chains of sugars and having a specific three-dimensional structure and/or a specific characteristic charge.

The methods of isolating and/or purifying immunoglobulins, the methods for determining the length of the heavy chain of immunoglobulins and the methods of determining the life span of IgG3s in serum are known to the person skilled in the art working in the field of immunology. By way of illustration, various methods and protocols which can be used are described in "Current Protocols in Immunology", updated annually (4 volumes), published by the "National Institutes of Health", by John E. Coligan, Ada M. Kruisbeek, David H. Margulies, Ethan M. Shevach, Warren Strober—Wiley Interscience.

By way of illustration, the purification of the IgG3s of the present invention is carried out using immunoaffinity columns Hitrap™ Protein G HP (ref. 17-0404-01) and Hitrap™ Protein A HP (ref. 17-0402-01) from Amersham-Pharmacia. Once the serum/plasma has passed through the Hitrap™ Protein A HP column, which binds only the IgG1s, IgG2s and IgG4s, the serum/plasma which has had the IgG1s, IgG2s and IgG4s removed is passed through the Hitrap™ Protein G HP column in order to purify the IgG3s.

The molecular weight of the heavy and light chains of the IgGs is determined for example by electrophoresis on a 12% polyacrylamide gel (Ready Gel Tris-HCl glycine BIORAD ref. 161-0901). In brief, the IgG3s purified on the immunoaffinity column are reduced by heating for 3 minutes at 95° C. in the presence of a reducing buffer (Laemmli sample Buffer BIORAD ref. 161-0737 +β mercaptoethanol) then loaded onto the gel. Migration takes place within 40 minutes at 200 V, 35 mA. The gels are dyed using a commercial solution (Bio-Safe Coomassie BIORAD, ref. 161-0786).

Finally, the life span of the variant IgG3s is determined by an ELISA test carried out each month or each quarter in the serum or plasma of non-progressor patients, making it possible to confirm the presence of IgG3.

By isolation of the variant immunoglobulin IgG3 according to the invention, the preparation of monoclonal antibodies of variant IgG3 type is also covered. In order to prepare monoclonal antibodies or fragments thereof, reference may be made to the techniques which are described in particular in the manual "Antibodies" (Harlow et al., 1988) or to the technique for preparation from hybridomas described by Kohler and Milstein in 1975. The monoclonal antibodies according to the invention may be obtained for example from cells of an animal immunized against the gp160 protein, or one of the fragments thereof, and comprising the R7V epitope. The antibody according to the invention may be purified for example on an affinity column on which the target epitope or antigen has been immobilized beforehand, for example the R7V epitope of the gp160 protein of HIV.

The inventive concept on which the invention is based cannot be reduced solely to the immunoglobulin IgG3s purified and/or isolated from patients suffering from AIDS. This is because the variant immunoglobulin IgG3s demonstrated by the inventors are also expressed in the serum of patients suffering from other pathologies involving a viral infection. Among these pathologies involving a viral infection, mention may be made by way of non-exhaustive examples of the pathologies associated with human T-cell leukaemia viruses (HTLV), the cytomegalovirus (CMV), herpes viruses (HSV-1, HSV-2), the Epstein Barr virus (EBV) and hepatitis viruses (HBV, HBC). The invention also relates to the variant immunoglobulin IgG3s isolated and/or purified from a patient suffering from an infectious disease of variable development, for instance neurological diseases such as multiple sclerosis, skin diseases such as psoriasis, auto-immune diseases such as systemic lupus erythematosus, and cancers of retroviral origin such as familial inflammatory breast cancer.

The invention also covers the fragments of variant immunoglobulin IgG3. The antibody fragments according to the invention comprise any fragment of said antibody capable of binding to the epitope of the protein to which there binds the antibody from which said fragment comes. Examples of such fragments include in particular single-chain antibodies or monovalent fragments Fab or Fab' and divalent fragments such as F(ab')2, which have the same binding specificity as the antibody from which they come. A fragment according to the invention may also be a single-chain Fv fragment. Antibody fragments of the invention may be obtained from immunoglobulins according to the invention by methods such as digestion by enzymes, such as pepsin or papain, and/or by cleavage of the disulphide bridges by chemical reduction. Alternatively, following sequencing of the primary structure of the variant IgG3 according to the invention, the antibody fragments may be synthesized by automatic peptide synthesizers such as those supplied by the company Applied Biosystems for example.

The present invention also relates to antisera comprising the immunoglobulin according to the invention.

The person skilled in the art has at his disposition the molecular and cell biology tools for carrying out the cloning, sequencing and expression, by the recombinant route, of the variant immunoglobulin IgG3s (Sambrook et al., 1989; Coligan et al., Current Protocols in Immunology, see page 6). These recombinant IgG3s, which are also within the scope of the present invention, could thus be produced in vitro and optionally modified by recombinant DNA technologies or chemistry technologies in order to give them particular properties.

Depending on the desired diagnostic applications, the antibody according to the invention or one of the fragments thereof may be immobilized on a support. The immobilization or coupling may be carried out on many supports known to the person skilled in the art. This immobilization or coupling is preferably carried out on a solid support either directly or indirectly via a spacer arm. The solid supports may in particular include glass, polystyrene, polypropylene, polyethylene, dextran, nylon, or natural or modified celluloses. These supports may be either soluble or insoluble.

For other applications, the antibody according to the invention or one of the fragments thereof may be labelled directly or indirectly by a marker so as to obtain a conjugate that makes it possible to generate a detectable and/or quantifiable signal that can be used for in vivo or in vitro diagnosis. The corresponding diagnostic kit comprising the labelled antibody, or one of the fragments thereof, is also one of the subjects of the present invention. The marker may be selected from enzymes, dyes, haptenes, luminescent agents such as radioluminescent, chemiluminescent, bioluminescent, fluorescent and phosphorescent agents, ligands such as biotin, avidin, streptavidin, digoxigenin, and radioactive isotopes. Thus, the immunoglobulin according to the invention or one of the labelled fragments thereof is conjugated for example with enzymes such as peroxidase, alkaline phosphatase, β-D-galactosidase, glucose oxidase, glucose amylase, carbonic anhydrase, acetyl cholinesterase, lysozyme, malate dehydrogenase or glucose-6-phosphate dehydrogenase, or with a molecule such as biotin, digoxigenin or 5-bromo-deoxyuridine. Fluorescent markers may also be conjugated to the immunoglobulin or one of the fragments thereof according to the invention and include for example fluorescein and its derivatives, rhodamine, Texas red, dansyl, umbelliferone and autofluorescent proteins such as GFP ("Green Fluorescent Protein"), etc. Other conjugates may also include chemiluminescent markers such as luminol and dioxetanes or bioluminescent markers such as luciferase and luciferin.

Among the radioactive isotopes which can be bound to the immunoglobulin or one of the fragments thereof according to the invention, preference is also given to the radioactive markers such as $^{14}C$, $^{36}Cl$, $^{57}Co$, $^{58}Co$, $^{51}Cr$, $^{152}Eu$, $^{59}Fe$, $^{3}H$, $^{125}I$, $^{131}I$, $^{32}P$, $^{35}S$, $^{75}Se$ and $^{99m}Tc$, which can be detected by known means such as the gamma-ray counter or scintillation counter, by autoradiography, etc. The present invention also comprises the conjugates whose detectable marker is selected from the markers which can be used in in vivo imaging. Examples of such markers according to the invention are $^{72}As$, $^{67}Cu$, $^{67}Ga$, $^{68}Ga$, $^{123}I$, $^{125}I$, $^{131}I$, $^{111}In$, $^{97}Ru$, $^{99m}Tc$, $^{201}Tl$ and $^{89}Zr$. The invention also includes the paramagnetic isotopes used in magnetic resonance imaging (MRI), which include in particular $^{52}Cr$, $^{162}Dy$, $^{56}Fe$, $^{157}Gd$ and $^{55}Mn$. The term "in vivo imaging" must be understood in the present description to mean any method which makes it possible to detect a labelled antibody according to the present invention or one of the fragments thereof which binds specifically to the epitope of the protein of interest in the body of the patient. The patient will preferably be a man liable to have cells infected by a virus or suffering from an infectious disease of variable development, abnormally expressing the protein of interest.

Such conjugates may be prepared by methods known to the person skilled in the art. They may be coupled to the markers directly or by way of an intermediate functional group, a spacer group or a linkage group such as a polyaldehyde, for instance glutaraldehyde, ethylenediamine-tetraacetic acid (EDTA), diethylenetriaminepentaacetic acid (DPTA), or in the presence of coupling agents such as periodate, benzoquinone, etc. Conjugates comprising markers of fluorescein type may be prepared by reaction with an isothiocyanate.

One of the objects of the present invention is also to provide a method for the diagnosis and/or in vitro dosage of a pathology selected from viral infections and infectious diseases of variable development, comprising the steps (i) contacting a sample of body fluid and/or body tissue, from a patient in which the presence of said pathology is suspected, with an immunoglobulin, a fragment of immunoglobulin or an antiserum according to the invention; and (ii) detecting the presence of an immune complex between said immunoglobulin and a specific epitope of said pathology. The term body fluid or biological fluid is understood to mean fluids such as serum, total blood, urine, sperm, cells, a tissue sample or biopsies of human origin. There are many methods for detecting the immune complex, these being known to the person skilled in the art; they depend on the nature of the diagnosis and the dosage to be carried out. This may be the ELISA test, RIA, a sandwich method, an immunoprecipitation, an agglutination test, a competition test, or any test known to the person skilled in the art which depends on the formation of an antibody-antigen immune complex. By way of example, one preferred method uses immunoenzymatic processes according to the ELISA technique, immunofluorescence processes, radioimmunological (RIA) processes, or equivalents thereof. All these methods are preferably based on the binding of the immunoglobulins in question to antigen peptides and then the demonstration of this binding.

More particularly, the invention also covers a method for the diagnosis and/or in vitro dosage of the human acquired immune deficiency syndrome (AIDS), comprising the steps (i) contacting a sample of body fluid and/or body tissue, from a patient in which the presence of HIV is suspected, with an immunoglobulin, a fragment of immunoglobulin or an antiserum according to the invention, and (ii) detecting the presence of an immune complex between said immunoglobulin and the gp160 protein of HIV, and in particular the R7V epitope of this protein contained in said sample.

The invention also relates to an in vitro or in vivo method for treating biological fluid of a patient suffering from a pathology selected from viral infections, in particular HIV, and infectious diseases of variable development, said method comprising the step of contacting an effective amount of immunoglobulin, a fragment of immunoglobulin or an antiserum according to the invention with said biological fluid, so as to neutralize a specific epitope of the pathology in said fluid. The method moreover optionally comprises the additional step of removing from the reaction mixture the immune complex thus formed. Within the context of an in vitro method for treating biological fluid, the method may furthermore comprise the additional step of reinjecting into the patient all or part of the biological fluid thus treated. Neutralization of the HIV virus, for example, is understood to refer to any mechanism which has the in vivo effect of destroying and/or preventing the propagation of viruses. The variant immunoglobulin IgG3 according to the invention appears to constitute, given its G3 subtype and its stability, an excellent means for neutralizing any body fluid intended to be reinoculated or reintroduced into an individual, such as the blood of an HIV-positive man for giving a blood transfusion to an individual, a tissue of an HIV-positive man in the case of a tissue graft, or the sperm of an HIV-positive man for inseminating an HIV-negative woman. This is because, since the IgG3 subtype binds the complement, the immunoglobulins according to the invention induce the lysis of the infected cells.

According to one particular embodiment, the invention provides an in vitro method for neutralizing cells infected with HIV in a biological sample of body fluid and/or body tissue from an HIV-positive patient. This method comprises the following steps:

(i) combining simultaneously, separately or sequentially the immunoglobulin or one of the fragments thereof or the antiserum according to the invention with the biological sample containing the cells infected with HIV having the gp160 protein at their surface and with protein G bound to magnetic particles;

(ii) incubating the mixture obtained in (i) under conditions which allow the binding of said immunoglobulin to the gp160 protein, and preferably to the R7V epitope, so as to form a complex, said complex comprising said antibody bound to an HIV-infected cell fixed to this magnetic particle;

(iii) displacing this magnetic particle to a predetermined point of the container containing this reaction mixture, such that the displacement is brought about by a magnetic field acting on said magnetic particle.

The invention also covers an in vitro method for diagnosing a non-progressor patient suffering from a pathology selected from viral infections, in particular AIDS, and infectious diseases of variable development, characterized in that the presence of immunoglobulin IgG3 is detected, preferably by means of an immunological test, said immunoglobulin IgG3 having the following characteristics (i) a life span in the serum of the patient that is greater than that of the IgG3s that are normally present, and in particular of at least 15 days, preferably at least one month, (ii) a heavy chain, the molecular weight of which, determined by electrophoretic mobility, is less than the molecular weight of the IgG3s normally present in human serum (60 kDa), said heavy chain having a molecular weight of about 50 kDa and comprising the complement binding site, and (iii) optionally having a serum concentration that is at least once as great, at least twice as great or at least three times as great (i.e. 1 g/L) as the IgG3 concentration of a normal serum. The diagnostic test used is preferably selected from an ELISA test, RIA, a sandwich method, an immunoprecipitation or an agglutination test. This diagnostic method for detecting the IgG3 variant according to the invention is of considerable interest. This is because the HIV-positive patients who carry this IgG3 variant are non-progressors. In this case, diagnosis is very favourable and it is possible to avoid heavy therapeutic treatments. This is particularly true in the case of a pregnancy where the presence of these antibodies in the mother (HIV+) appears to lead to non-infection in then newborn child. The present invention therefore aims to use the variant immunoglobulin IgG3 or one of the fragments thereof or the antiserum according to the invention as a protective marker in pathologies selected from viral diseases, in particular AIDS, and infectious diseases of variable development.

More generally, the present invention aims to cover the use of an immunoglobulin or one of the fragments thereof or an antiserum according to the invention to carry out an immunological test selected from the ELISA test, the RIA test, the sandwich method, immunoprecipitation or the agglutination test.

The present invention also aims to cover the use of the immunoglobulin according to the invention as a medicament, and more precisely as a therapeutic antibody or as a targeting agent. The term therapeutic antibody is understood to mean immunoglobulin IgG3s or a serum or plasma containing them, injected intravenously into progressor patients in respect of whom conventional therapy is generally not successful.

The variant immunoglobulin IgG3 or the antiserum containing it can be used to prepare a medicament intended for the therapeutic treatment and/or prophylaxis of a viral disease, in particular AIDS, but also diseases of which the causative agent is a virus as listed above. When the disease is AIDS, the variant immunoglobulin IgG3 used to prepare a medicament intended to neutralize the HIV gp160 protein in a man suffering from AIDS is preferably directed against the R7V epitope of the gp160 protein of HIV. The variant immunoglobulin IgG3 or the antiserum containing it can also be used to prepare a medicament intended for the therapeutic treatment and/or prophylaxis of an infectious disease of variable development.

The immunoglobulin IgG3 or one of the fragments thereof according to the invention may be used as a medicament in the form of a mixture with at least one anti-retroviral agent selected from the group comprising reverse transcriptase and/or viral antiprotease inhibitors as a combination product for simultaneous use, separate use or sequentially use in antiviral therapy. The reverse transcriptase inhibitor is preferably selected from 3'-azido-3'-deoxythymidine (AZT), 2',3'-dideoxyinosine (ddI), 2',3'-dideoxycytidine (ddC), (−) 2',3'-dideoxy-3'-thiacytidine (3TC), 2',3'-didehydro-2',3'-dideoxythymidine (d4T) and (−)2'-deoxy-5-fluoro-3'-thiacytidine (FTC), TIBO, HEBT, TSAO, α-APA, nevirapine, BAHP, phosphonoformic acid (PFA); the viral antiprotease is selected from indinavir and saquinavir.

In the context of a use of the antibody as a targeting agent, said antibody is optionally modified by chemistry technologies and/or recombinant DNA technologies, in order to modify its stability, its affinity, its bioavailability or its compatibility, etc. The immunoglobulin according to the invention as a targeting agent is conjugated directly or indirectly to at least one agent selected from the group comprising antiproliferative agents, antineoplastic agents or cytotoxic agents. Included among the agents which may be conjugated to the antibodies according to the invention are, besides the radioisotopes and the markers described above in particular, alkylating compounds such as mechlorethamine, triethylene phosphoramide, triaziquone, camustine, semustine, methotrexate, mercaptopurine, cytarabine, fluorouracil, antibiotics such as actinomycin, hormones or hormone antagonists such as corticosteroids, for instance prednisone or progestins, bacterial or viral toxins. In one particular embodiment, the non-isotopic antiproliferative and/or antineoplastic and/or cytotoxic agent is a nucleic acid molecule such as, for example, single-stranded DNA, double-stranded DNA, single-stranded RNA, in particular an antisense RNA, double-stranded RNA or an RNA/DNA hybrid. This nucleic acid optionally encodes for a protein product of interest.

It also falls within the scope of the invention to provide a vaccine or pharmaceutical composition for the treatment or prevention of a pathology selected from viral infections and infectious diseases of variable development, comprising an immunoglobulin antibody or an antiserum according to the invention in association with a pharmaceutically acceptable carrier, excipient or diluent. The pharmaceutically acceptable excipients include, in particular, water, saline solutions, buffers or any other compound described for example in the Merck Index.

The compositions or vaccine according to the invention may also comprise components which increase the immunogenicity, in particular specific or non-specific immunity adjuvants such as Freund's adjuvant, polysaccharides or equivalent compounds. These are compounds known to the person skilled in the art in the field of vaccination. The compositions may be in any form whatsoever that is compatible with the selected route of administration. The administration of these compounds to the patient may be local or systemic and may be carried out by the intravenous, intra-arterial, intramuscular or intraperitoneal route, by way of the spinal fluid, or by the intradermal, oral, nasal, anal route. However, the compositions according to the present invention could be used by other routes, in particular by the aerosol route, in order to induce protection of the mucous membranes.

The amount of variant immunoglobulin IgG3s, or one of the fragments thereof, comprised in the pharmaceutical compositions according to the present invention and necessary for effective therapy will depend on various factors such as the mode of administration, the part of the body targeted, the physiological condition and the age of the patient, any side effects, counter-indications if there are any, concomitant therapies or other variables that a person skilled in the art will know how to adjust. The dosage for such therapeutic prevention or treatment will be carried out in such a way as to optimize the safety and effectiveness thereof. In general, the dosages used in vitro may provide an indication of the quantities used for administering the antibody in situ and thus use may be made of animal models to determine the effective quantities of immunoglobulins according to the invention for the treatment of a particular pathology, in particular AIDS.

The monoclonal antibodies or fragments thereof according to the invention also constitute a means of immunocytochemical or immunohistochemical analysis for analysing the expression of the protein of interest on electrophoresis gels or transfer membranes or specific tissue sections, for example by immunofluorescence or by radioactive or gold enzyme labelling. They make it possible in particular to demonstrate and quantify the specific normal or abnormal presence of the protein of interest in tissues or biological samples, which makes them useful for identifying and locating the expression of the protein of interest, for diagnosing pathologies associated with the abnormal presence of the protein of interest, such as for example gp160, but also for monitoring the development of methods for preventing or treating a pathology requiring said detection or said dosage. More generally, the antibodies, the fragments thereof or the antiserum according to the invention may advantageously be used in any situation where the expression of a protein of interest, for example the gp160 protein containing the R7V epitope, must be observed in a qualitative and/or quantitative manner.

Other features and advantages of the invention will emerge from the following description with the examples and the figures, the legends of which are given below.

EXAMPLES

Example 1

Demonstration of IgG3 Variants in Certain Individuals Infected with HIV and Qualified as Non-Progressors The immunoglobulin antibodies are divided into four subclasses, and generally the antibodies induced after immunization belong to the $IgG_1$s, which have a very long half-life.

The inventors describe here, in patients infected with HIV, the presence of protective antibodies associated with $IgG_3$s, whereas the antibodies which indicate infection are always $IgG_1$s. An $IgG_3$ variant exists in some individuals who are infected with HIV and are qualified as non-progressors.

1.1. The IgG3 Variant has a Life Span of Several Months

This variant differs from the conventional $IgG_3$s in terms of its half-life; the half-life is seven days for conventional $IgG_3$s and several months for the variant, as shown by the study on the patient sequential follow-ups, the serums being sampled at intervals of several months (Table 1).

Table 1 shows the results of an ELISA test searching for protective antibodies directed against an epitope associated with HIV, called R7V. These antibodies are revealed by second antibodies which distinguish the various subclasses of human immunoglobulins.

The anti-R7V protective antibodies are always $IgG_3$s and/or $IgG_4$s, but never $IgG_1$s or $IgG_2$s, and their high titre remains over several months.

TABLE 1

Study of the anti-R7V IgG subclasses of sequential serums

| Dates samples were taken | $IgG_{1+2}$ | $IgG_3$ | $IgG_4$ |
| --- | --- | --- | --- |
| Positivity threshold = 0.1 | | | |
| Serum of patient 1 diluted ⅕ L | | | |
| Blank | 0.075 | 0.117 | 0.127 |
| Seronegative control | −0.005 | 0.031 | −0.012 |
| 02 Dec. 1993 | −0.004 | 0.002 | −0.011 |
| 05 Apr. 1994 | −0.002 | 0.216 | 0.025 |
| 28 Jul. 1994 | 0 | 0.456 | 0.028 |
| 10 Nov. 1994 | −0.004 | 0.070 | 0.029 |
| 09 Mar. 1995 | 0.0015 | 0.262 | 0.042 |
| 13 Jul. 1995 | −0.004 | 0.130 | 0.035 |
| 22 Feb. 1996 | −0.009 | 0.224 | 0.032 |
| 20 Jun. 1996 | −0.007 | 0.128 | 0.025 |
| 28 Nov. 1996 | −0.006 | 0.166 | 0.050 |
| 03 Mar. 1997 | −0.003 | 0.110 | −0.065 |
| 05 Jun. 1997 | −0.005 | 0.085 | −0.069 |
| 15 Dec. 1997 | −0.007 | 0.073 | −0.069 |
| 11 May 1998 | −0.008 | 0.090 | −0.069 |
| 25 Sep. 1998 | −0.002 | 0.153 | −0.063 |
| 11 Oct. 1999 | −0.004 | 0.148 | −0.067 |
| 11 Jan. 2001 | −0.006 | 0.133 | −0.069 |
| Positivity threshold = 0.1 | | | |
| Serum of patient 2 diluted ⅕ L | | | |
| Blank | 0.075 | 0.117 | 0.127 |
| Seronegative control | −0.005 | 0.031 | −0.012 |

TABLE 1-continued

Study of the anti-R7V IgG subclasses of sequential serums

| Dates samples were taken | $IgG_{1+2}$ | $IgG_3$ | $IgG_4$ |
|---|---|---|---|
| 01 Jul. 1993 | −0.004 | 0.565 | −0.068 |
| 11 Oct. 1993 | −0.003 | 0.381 | −0.066 |
| 17 Jan. 1994 | −0.002 | 0.418 | −0.065 |
| 02 May 1994 | −0.006 | 0.442 | −0.068 |
| 01 Aug. 1994 | −0.008 | 0.419 | −0.069 |
| 05 Dec. 1994 | −0.003 | 0.455 | −0.062 |
| 10 Apr. 1995 | −0.005 | 0.440 | −0.065 |
| 03 Jul. 1995 | −0.007 | 0.397 | −0.068 |
| 30 Oct. 1995 | −0.004 | 0.726 | −0.072 |
| 29 Jan. 1996 | 0 | 0.641 | −0.065 |
| 06 May 1996 | −0.006 | 0.544 | −0.068 |
| 19 Sep. 1996 | −0.007 | 0.491 | −0.067 |
| 20 Jan. 1997 | −0.009 | 0.374 | −0.064 |
| 06 Oct. 1997 | −0.002 | 0.394 | −0.064 |
| 12 Jan. 1998 | −0.005 | 0.558 | −0.066 |
| 19 Mar. 1998 | −0.007 | 0.532 | −0.068 |
| 22 Jun. 1998 | −0.007 | 0.503 | −0.074 |
| 28 Sep. 1998 | −0.004 | 0.457 | −0.062 |
| 01 Feb. 1999 | −0.006 | 0.230 | −0.067 |
| 26 Apr. 1999 | −0.01 | 0.086 | −0.064 |
| 15 Jul. 1999 | −0.013 | 0.060 | −0.066 |
| 16 Dec. 1999 | 0.099 | 0.079 | −0.061 |
| 23 Mar. 2000 | 0.084 | 0.058 | −0.064 |

1.2. The IgG3 Variant has a Heavy Chain of Approximately 50 kDa

The electrophoretic analyses of FIG. 1 show that the $IgG_3$ variant present in non-progressor HIV-infected patients has a heavy chain with greater electrophoretic mobility, which means that its molecular weight is lower than that of a conventional $IgG_3$ purified in a normal HIV-negative subject.

FIGS. 1a to 1e show the migration of the $IgG_3$s purified either from normal HIV-negative subjects or from HIV-positive patients on a 12% polyacrylamide gel. The heavy chains have a molecular weight of around 50 kDa, whereas the light chains have a molecular weight of 25 kDa. (Molecular weight markers: $M_1$: 250; 150; 100; 75; 50; 37; 25; 15; 10 kDa/$M_2$: 200; 116; 97; 66; 45; 31; 21.5; 14.4; 6.5 kDa).

The $IgG_3$ variant is recognized by antibodies directed either against the Fab part of the $IgG_3$s or antibodies directed against the hinge part. The variation should therefore concern the Fc fragment, probably at the glycosylation level.

1.3. The $IgG_3$ Variant is Found in Most Non-Progressor HIV-Positive Patients (Table 2).

TABLE 2

Determination of the anti-R7V IgG subclass by ELISA
Positivity threshold = 0.2

| | $IgG_1$ | $IgG_2$ | $IgG_3$ | $IgG_4$ |
|---|---|---|---|---|
| Blank | | | | |
| | 0.058 | 0.056 | 0.085 | 0.081 |
| Seronegative control 1/50 | | | | |
| | 0.059 | 0.060 | 0.113 | 0.091 |
| Positive control | | | | |
| | 0.057 | 0.057 | 0.854 | 0.084 |
| 1 ALB HE 1/50 (07 Jan. 1994) | 0.072 | 0.063 | 0.080 | 0.073 |
| 2 ANO MA 1/50 (13 Nov. 2000) | 0.061 | 0.057 | 0.136 | 0.108 |
| 3 ARG CH 1/50 (30 Nov. 2000) | 0.058 | 0.055 | 0.481 | 0.071 |

TABLE 2-continued

Determination of the anti-R7V IgG subclass by ELISA
Positivity threshold = 0.2

| | $IgG_1$ | $IgG_2$ | $IgG_3$ | $IgG_4$ |
|---|---|---|---|---|
| Blank | | | | |
| | 0.058 | 0.056 | 0.085 | 0.081 |
| Seronegative control 1/50 | | | | |
| | 0.059 | 0.060 | 0.113 | 0.091 |
| Positive control | | | | |
| | 0.057 | 0.057 | 0.854 | 0.084 |
| 4 AUC LA 1/50 (15 Nov. 1999) | 0.065 | 0.061 | 0.112 | 0.138 |
| 5 AUR PH 1/50 (03 Jan. 1994) | 0.069 | 0.064 | 0.343 | 0.685 |
| 6 BEN MI 1/50 (14 Feb. 2000) | 0.062 | 0.064 | 0.077 | 0.071 |
| 7 BER YV 1/50 (13 Mar. 2000) | 0.105 | 0.073 | 0.109 | 0.307 |
| BER YV 1/50 (25 Nov. 1999) | 0.102 | 0.072 | 0.107 | 0.339 |
| 8 BITT MA 1/50 (27 May 1999) | 0.060 | 0.054 | 0.384 | 0.091 |
| 9 BOI CH 1/50 (27 Nov. 2000) | 0.060 | 0.055 | 0.236 | 0.092 |
| 10 BOU NA 1/50 (23 Dec. 1999) | 0.070 | 0.067 | 0.119 | 0.081 |
| 11 CAM GE 1/50 (27 Dec. 2000) | 0.063 | 0.072 | 0.079 | 0.077 |
| 12 COU DI 1/50 (16 Sep. 1998) | 0.094 | 0.073 | 0.081 | 2.468 |
| COU DI 1/50 (09 Mar. 2000) | 0.074 | 0.070 | 0.077 | 1.935 |
| COU DI 1/50 (08 Sep. 2000) | 0.058 | 0.059 | 0.059 | 2.641 |
| 13 CUC JE 1/50 (28 Sep. 2000) | 0.059 | 0.056 | 0.173 | 0.088 |
| 14 DAN NO 1/50 (28 Sep. 2000) | 0.073 | 0.066 | 0.083 | 0.094 |
| 15 DAR DO 1/50 (10 Mar. 1994) | 0.078 | 0.066 | 0.795 | 0.085 |
| 16 DOM JO 1/50 (13 Jul. 1992) | 0.060 | 0.057 | 0.275 | 0.096 |
| 17 ESM GU 1/50 (18 Dec. 2000) | 0.061 | 0.064 | 0.083 | 0.119 |
| 18 ETC MA 1/50 (25 Sep. 1998) | 0.114 | 0.067 | 1.266 | 0.089 |
| ETC MA 1/50 (13 Jun. 2000) | 0.057 | 0.057 | 0.854 | 0.084 |
| 19 FER JE 1/50 (26 Jun. 2000) | 0.064 | 0.070 | 0.079 | 0.204 |
| 20 FIN RO 1/50 (13 Nov. 2000) | 0.063 | 0.065 | 0.097 | 0.089 |
| 21 FON RE 1/50 (29 Jun. 2000) | 0.083 | 0.053 | 0.095 | 0.070 |
| 22 GEM SA 1/50 (20 Oct. 1998) | 0.093 | 0.071 | 0.090 | 0.086 |
| GEM SA 1/50 (29 Apr. 1999) | 0.060 | 0.061 | 0.114 | 0.080 |
| GEM SA 1/50 (07 Jun. 2000) | 0.078 | 0.050 | 0.079 | 0.068 |
| 23 GOU JE 1/50 (13 Jun. 2000) | 0.069 | 0.052 | 0.098 | 0.072 |
| 24 KAZ AL 1/50 (20 Jan. 2001) | 0.059 | 0.065 | 0.117 | 0.080 |
| 25 KOH MI 1/50 (05 Aug. 1994) | 0.056 | 0.056 | 0.869 | 0.088 |
| 26 MAN GU 1/50 (06 Apr. 2000) | 0.074 | 0.053 | 0.072 | 0.079 |
| 27 MART DO 1/50 (03 May 2000) | 0.082 | 0.064 | 0.311 | 0.077 |
| MART DO 1/50 (09 May 1994) | 0.082 | 0.067 | 0.329 | 0.079 |
| 28 MART PA 1/50 (13 Jun. 2000) | 0.055 | 0.058 | 0.106 | 0.083 |
| 29 MEC EV 1/50 (28 Jan. 2000) | 0.068 | 0.054 | 0.086 | 0.074 |
| 30 MEN CH 1/50 (09 Mar. 2000) | 0.051 | 0.053 | 0.078 | 0.155 |
| 31 MOR AN 1/50 (20 Apr. 2000) | 0.075 | 0.065 | 0.109 | 0.086 |
| 32 PAT MA 1/50 (09 Jul. 1998) | 0.086 | 0.072 | 0.116 | 0.085 |
| PAT MA 1/50 (07 Jul. 2000) | 0.054 | 0.053 | 0.104 | 0.070 |
| PAT MA 1/50 (11 Jun. 1991) | 0.082 | 0.067 | 0.152 | 0.067 |
| 33 REF EL 1/50 (28 Sep. 2000) | 0.070 | 0.067 | 0.085 | 1.153 |
| 34 RIG ST 1/50 (02 Feb. 1998) | 0.089 | 0.070 | 0.131 | 0.096 |
| 35 RIO EM 1/50 (11 Jun. 1992) | 0.071 | 0.067 | 0.115 | 0.073 |
| 36 ROB IS 1/50 (26 Jun. 2000) | 0.054 | 0.056 | 0.095 | 0.068 |
| 37 ROD CH 1/50 (12 Apr. 1999) | 0.057 | 0.055 | 0.155 | 0.068 |
| 38 SAN FR 1/50 (19 Jun. 2000) | 0.059 | 0.054 | 0.139 | 0.088 |
| 39 SAU CH 1/50 (20 Dec. 1991) | 0.074 | 0.069 | 0.092 | 0.640 |
| SAU CH 1/50 (27 Nov. 2000) | 0.059 | 0.054 | 0.142 | 0.307 |
| 40 SEN BE 1/50 (22 Feb. 1991) | 0.058 | 0.057 | 0.143 | 0.082 |
| 41 SIL RE 1/50 (25 Aug. 2000) | 0.056 | 0.057 | 0.131 | 0.107 |
| 42 SIMO FR 1/50 (29 Jun. 2000) | 0.061 | 0.055 | 0.221 | 0.077 |
| 43 SLI ZB 1/50 (13 Nov. 2000) | 0.065 | 0.055 | 0.260 | 0.095 |
| 44 SOL EM 1/50 (27 Nov. 2000) | 0.056 | 0.059 | 0.180 | 0.143 |
| 45 TAR AL 1/50 (24 Jul. 1991) | 0.059 | 0.058 | 0.203 | 0.414 |
| 46 TEM ST 1/50 (10 May 1993) | 0.059 | 0.055 | 0.219 | 0.338 |
| TEM ST 1/50 (18 Nov. 1999) | 0.056 | 0.060 | 0.104 | 0.103 |
| 47 TER YV 1/50 (02 Jun. 1999) | 0.061 | 0.057 | 0.123 | 0.101 |
| TER YV 1/50 (28 Oct. 1999) | 0.104 | 0.076 | 0.122 | 0.412 |
| 48 THI SY 1/50 (05 Jun. 2000) | 0.056 | 0.062 | 0.096 | 0.089 |
| 49 THO EL 1/50 (04 Dec. 2000) | 0.077 | 0.066 | 0.115 | 1.189 |
| 50 THO MI 1/50 (08 Jun. 2000) | 0.057 | 0.057 | 0.146 | 0.078 |
| 51 THO PA 1/50 (04 Dec. 2000) | 0.075 | 0.073 | 0.088 | 0.080 |

TABLE 2-continued

Determination of the anti-R7V IgG subclass by ELISA
Positivity threshold = 0.2

|  | $IgG_1$ | $IgG_2$ | $IgG_3$ | $IgG_4$ |
|---|---|---|---|---|
| Blank | | | | |
|  | 0.058 | 0.056 | 0.085 | 0.081 |
| Seronegative control 1/50 | | | | |
|  | 0.059 | 0.060 | 0.113 | 0.091 |
| Positive control | | | | |
|  | 0.057 | 0.057 | 0.854 | 0.084 |
| 52 TOC RO 1/50 (23 Nov. 1992) | 0.058 | 0.056 | 0.095 | 0.097 |
| 53 TOC UR 1/50(23 Nov. 1992) | 0.064 | 0.057 | 0.106 | 0.136 |
| 54 VAL MAR 1/50 (12 Feb. 1992) | 0.060 | 0.058 | 0.098 | 0.084 |
| 55 VIA JE 1/50 (01 Jul. 1993) | 0.098 | 0.077 | 1.426 | 0.099 |
| VIA JE 1/50 (23 Mar. 2000) | 0.059 | 0.053 | 0.181 | 0.073 |

Thus, from reading the above table it seems that none of the sera tested has any anti-R7V antibodies of type $IgG_1$ or $IgG_2$. Of 28 different R7V-positive patients, 13 patients are $IgG_3$-positive (46.4%), 3 patients are $IgG_3$-positive and $IgG_4$-positive (10.7%) and 12 patients are $IgG_4$-positive (42.8%).

In any one patient, the same anti-R7V IgG subclass is always found, regardless of the date on which the sample is taken, when the response is positive (BER YV, COU DI, ETC MA, MART DO, SAU CH).

The subclass of antibodies directed against the envelope glycoprotein of the virus (gp160) was determined by means of an ELISA test (Table 3).

TABLE 3

Determination of the anti-gp160 IgG subclass
(Sanofi Diagnostics Pasteur Kit)
Positivity threshold = 0.09

|  | $IgG_1$ | $IgG_2$ | $IgG_3$ | $IgG_4$ |
|---|---|---|---|---|
| Blank | 0.065 | 0.062 | 0.060 | 0.067 |
| Seronegative control 1/5 | 0.058 | 0.059 | 0.066 | 0.069 |
| ARG CH 1/5 (30 Nov. 2000) | 0.355 | 0.061 | 0.328 | 0.076 |
| AUR PH 1/5 (03 Jan. 1994) | 1.645 | 0.068 | 0.160 | 0.781 |
| BER YV 1/5 (25 Nov. 1999) | 1.322 | 0.073 | 0.371 | 0.078 |
| CAM GE 1/5 (27 Nov. 2000) | 0.121 | 0.050 | 0.066 | 0.051 |
| COU DI 1/5 (16 Sep. 1998) | 1.659 | 0.064 | 0.479 | 0.162 |
| DAN NO 1/5 (28 Sep. 2000) | 0.855 | 0.058 | 0.361 | 0.069 |
| DAR DO 1/5 (31 Aug. 1998) | 1.102 | 0.064 | 0.107 | 0.101 |
| ESM GU 1/5 (18 Dec. 2000) | 0.435 | 0.065 | 0.084 | 0.111 |
| ETC MA 1/5 (13 Jun. 2000) | 0.513 | 0.060 | 0.135 | 0.172 |
| FIN RO 1/5 (13 Nov. 2000) | 0.735 | 0.063 | 1.538 | 0.082 |
| GEM SA 1/5 (07 Jun. 2000) | 0.540 | 0.058 | 0.104 | 0.081 |
| MEN CH 1/5 (09 Mar. 2000) | 1.260 | 0.054 | 0.209 | 0.069 |
| PAT MA 1/5 (09 Jul. 1998) | 0.828 | 0.061 | 0.168 | 0.125 |
| REF EL 1/5 (28 Sep. 2000) | 1.511 | 0.073 | 0.252 | 0.080 |
| ROB IS 1/5 (26 Jun. 2000) | 0.182 | 0.049 | 0.076 | 0.052 |
| ROD CH 1/5 (12 Apr. 1999) | 0.952 | 0.059 | 0.154 | 0.071 |
| SAN FR 1/5 (19 Jun. 2000) | 1.112 | 0.063 | 0.157 | 0.076 |
| SAU CH 1/5 (27 Nov. 2000) | 0.122 | 0.06 | 0.062 | 1.297 |
| SOL EM 1/5 (27 Nov. 2000) | 0.191 | 0.056 | 0.106 | 0.062 |
| TEM ST 1/5 (18 Nov. 1999) | 0.834 | 0.061 | 0.069 | 0.082 |
| TER YV 1/5 (28 Oct. 1999) | 1.389 | 0.061 | 0.252 | 0.231 |
| THI SY 1/5 (05 Jun. 2000) | 0.633 | 0.063 | 0.088 | 0.088 |
| THO EL 1/5 (04 Dec. 2000) | 0.899 | 0.057 | 0.158 | 0.064 |
| THO MI 1/5 (08 Jun. 2000) | 0.151 | 0.053 | 0.082 | 0.059 |
| THO PA 1/5 (04 Dec. 2000) | 0.435 | 0.066 | 0.071 | 0.097 |
| TOC RO 1/5 (25 Nov. 1999) | 1.042 | 0.06 | 0.173 | 2.387 |
| VIA JE 1/5 (01 Jul. 1993) | 1.748 | 0.080 | 3.062 | 0.127 |

From reading this table, it seems that none of the sera tested has any anti-gp160 antibodies of type $IgG_2$. Of 27 different patients, 27 patients are $IgG_1$-positive (100%), 6 patients are only $IgG_1$-positive (22.2%), 10 patients are $IgG_1$-positive and $IgG_3$-positive (40.7%), 2 patients are $IgG_1$-positive and $IgG_4$-positive (7.4%) and 9 patients are $IgG_1$-positive, $IgG_3$-positive and $IgG_4$-positive (29.6%).

This experiment confirms the dispersion of the response in terms of antibodies directed against the envelope glycoprotein gp160 of the virion, and the constancy of the $IgG_3$s or $IgG_4$s in protected individuals.

Example 2

Immunoprecipitation of HIV with Total $IgG_3$s, Purified from Non-Progressor HIV-Positive Patients 2.1. Experimental Protocol:

A desired amount of pure HIV virus is added to a given amount of $IgG_3$ and the mixture is left to incubate for 1 hour at +4° C.

The following are then added:
either 50-100 μL of protein G bound to magnetic beads, and incubation is carried out for 1 hour at +4° C. (protein G binds the $IgG_1$, $IgG_2$, $IgG_3$ and $IgG_4$ antibodies)

or 50-100 μL of protein A bound to magnetic beads, and incubation is carried out for 1 hour at +4° C. (protein A binds the $IgG_1$, $IgG_2$ and $IgG_4$ antibodies but not the $IgG_3$s).

The beads fix to that wall of the tube which is closest to the applied magnetic field, and the protein G bead-$IgG_3$-virus complex can then be isolated. The virus bound to the antibodies is then demonstrated by measuring the viral protein P24 released after lysis of the virus from the immunoprecipitated virus (COULTER kit (6604535)) and/or by the RT-PCR technique for detecting viral RNA. (See FIG. 2).

2.2. Results

A typical experiment is shown in Table 4 where 65% of the virus is precipitated with 20 μg of IgG$_3$ from a non-progressor HIV-positive patient, whereas the IgG$_3$s of an HIV-negative individual have no effect.

TABLE 4

Immunoprecipitation (virus NDK/PBL of 29 Feb. 1996)

| Sample | % precipitation |
|---|---|
| 20 μg ARG CH IgG3 + 50 μL pure virus + 100 μL protein G | 64.70% |
| 10 μg ARG CH IgG3 + 50 μL pure virus + 50 μL protein G | 56.40% |
| 20 μg Seroneg. IgG3 + 50 μL pure virus + 100 μL protein G | 0.40% |
| 10 μg Seroneg. IgG3 + 50 μL pure virus + 50 μL protein G | 0.20% |
| virus control: 50 μL pure virus + 50 μL protein G | 0.10% |
| 20 μg ARG CH IgG3 + 50 μL pure virus + 100 μL protein A | 0.70% |
| 10 μg ARG CH IgG3 + 50 μL pure virus + 50 μL protein A | 0.70% |
| 20 μg Seroneg. IgG3 + 50 μL pure virus + 100 μL protein A | 0.20% |
| 10 μg Seroneg. IgG3 + 50 μL pure virus + 50 μL protein A | 0.40% |
| virus control: 50 μL pure virus + 50 μL protein A | 0.40% |

Figure 1A:
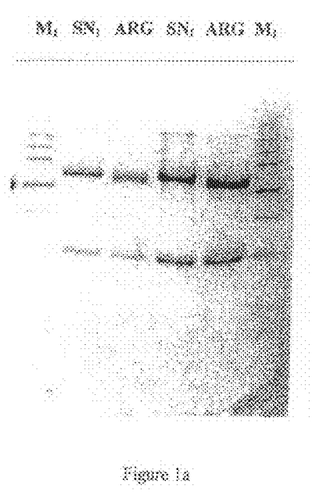
Figure 1B:
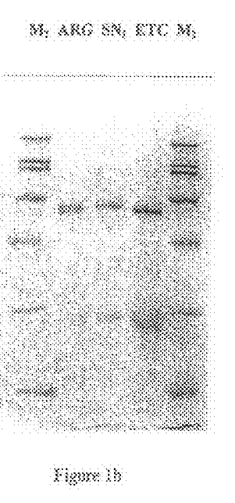
Figure 1C:
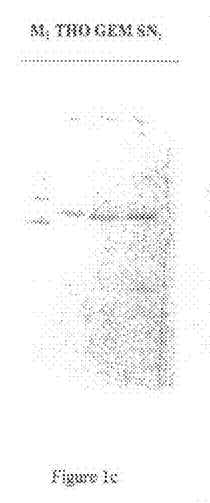
Figure 1D:
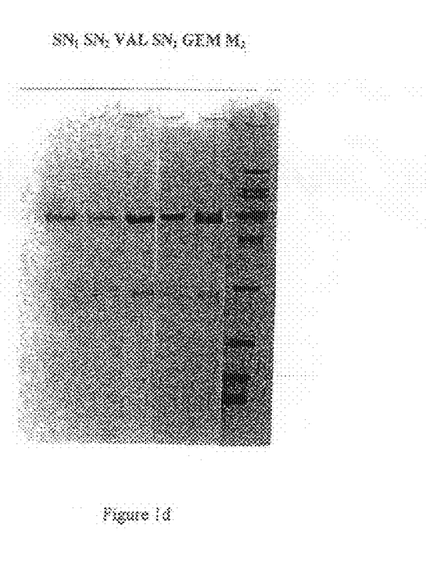
Figure 1E:
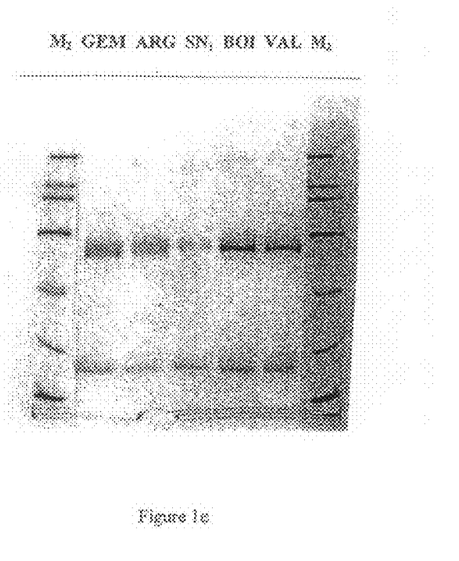
Figure 2:
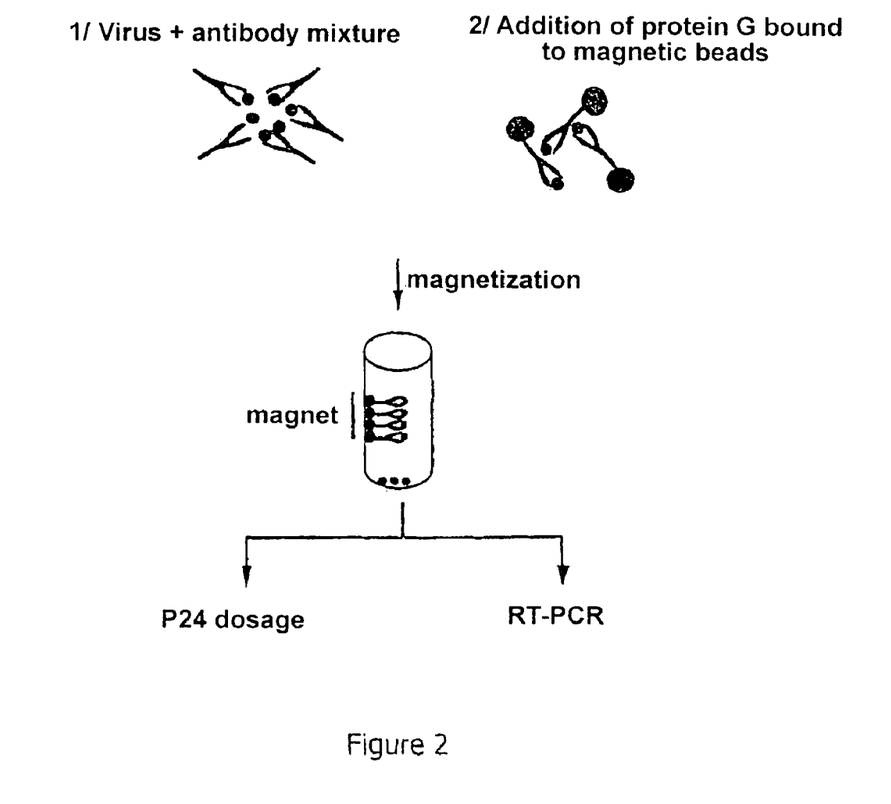
FIG. 2 is a diagram that shows a protocol for immunoprecipitation of the HIV retrovirus with the variant IgG3 by way of example.
Figure 3:
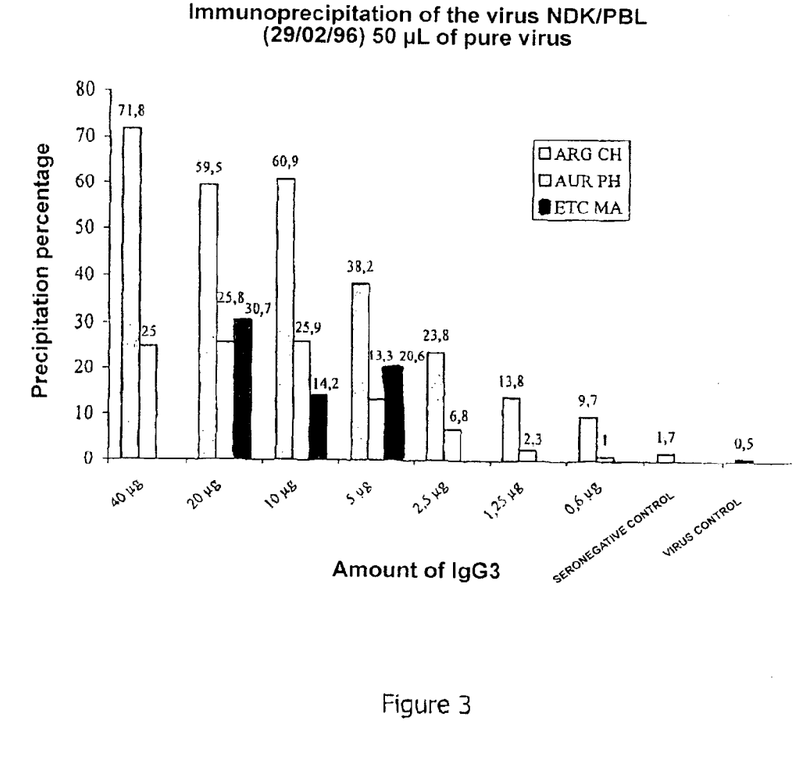
FIG. 3 is a bar graph that shows immunoprecipitation of the virus with the $IgG_3$s of three different patients.
Figure 4:
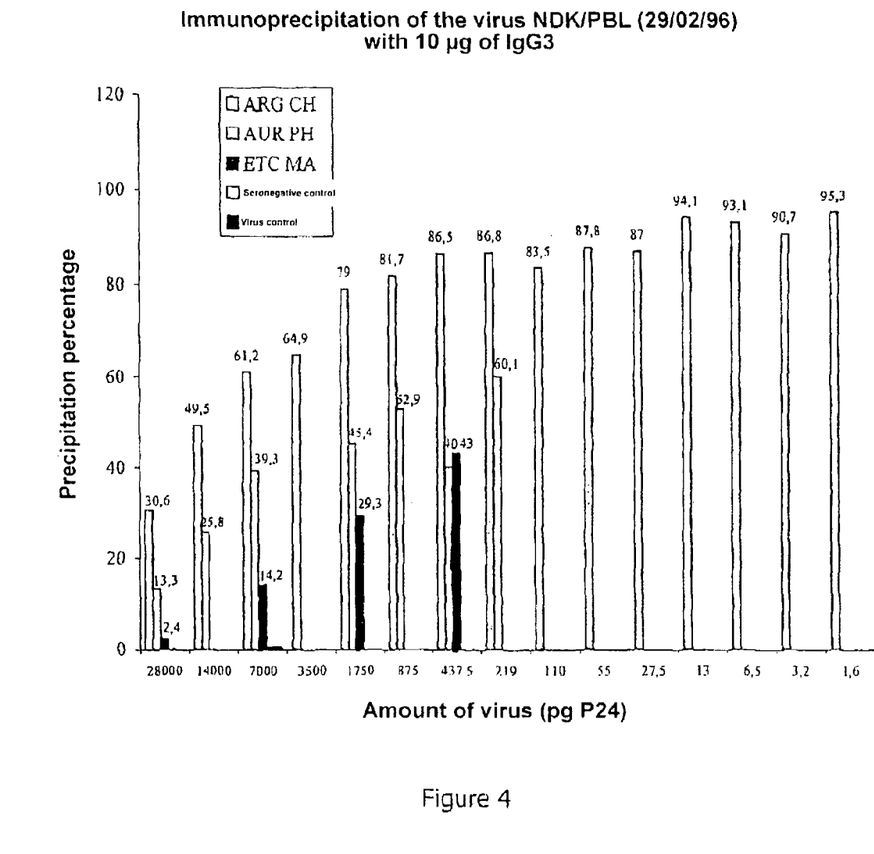
FIG. 4. is a bar graph that shows immunoprecipitation of variable amounts of virus with a fixed amount of IgG3 antibody.
Figure 5:
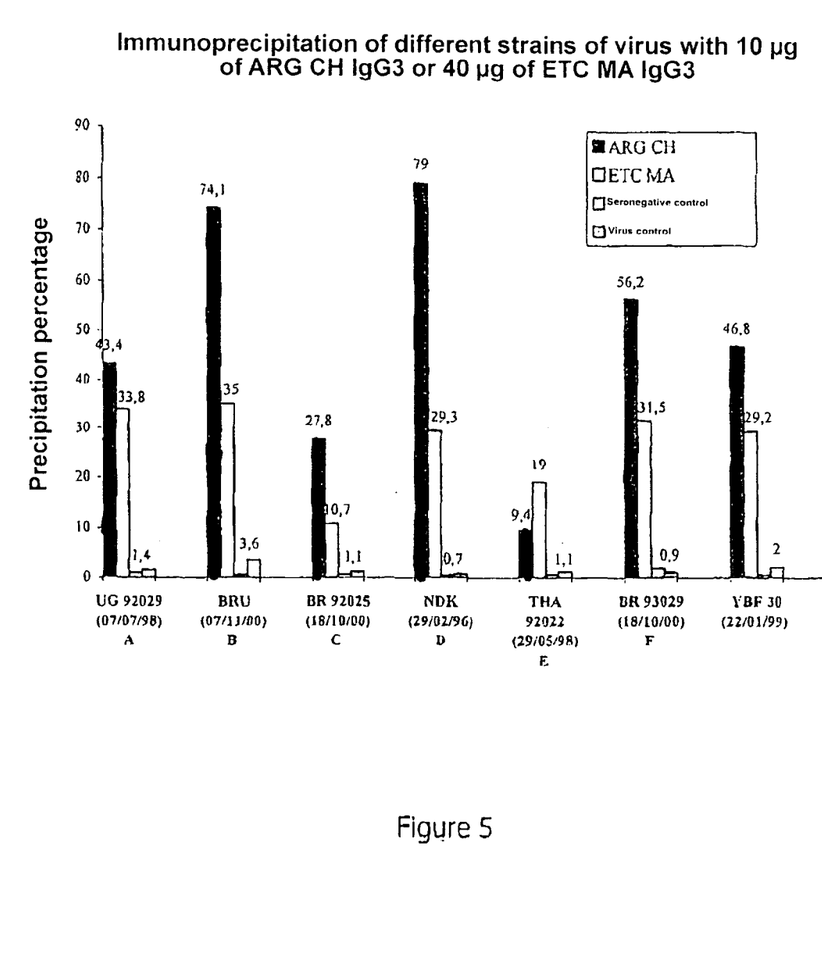
FIG. 5. is a bar graph that shows immunoprecipitation of different strains with a fixed amount of IgG3.

FIG. 3 shows the immunoprecipitation of the virus with the IgG$_3$s of three different patients. This immunoprecipitation of the virus for a fixed amount of virus is dose-dependent. FIG. 4 shows that with a fixed amount of IgG$_3$, it is possible to trap various virus dilutions. FIG. 5 shows that, regardless of the type of HIV, it is immunoprecipitated with the IgG$_3$s, here from three patients. The viral strains used are primary isolates having as phenotype clades A to F or a strain YBF 30 which is neither O nor M.

These experiments confirm that it is possible to isolate a virus by immunoprecipitation from IgG$_3$s purified by protein G.

Example 3

Neutralization of HIV by Total IgG$_3$s, Purified from Non-Progressor HIV-Positive Patients

Figure 6:
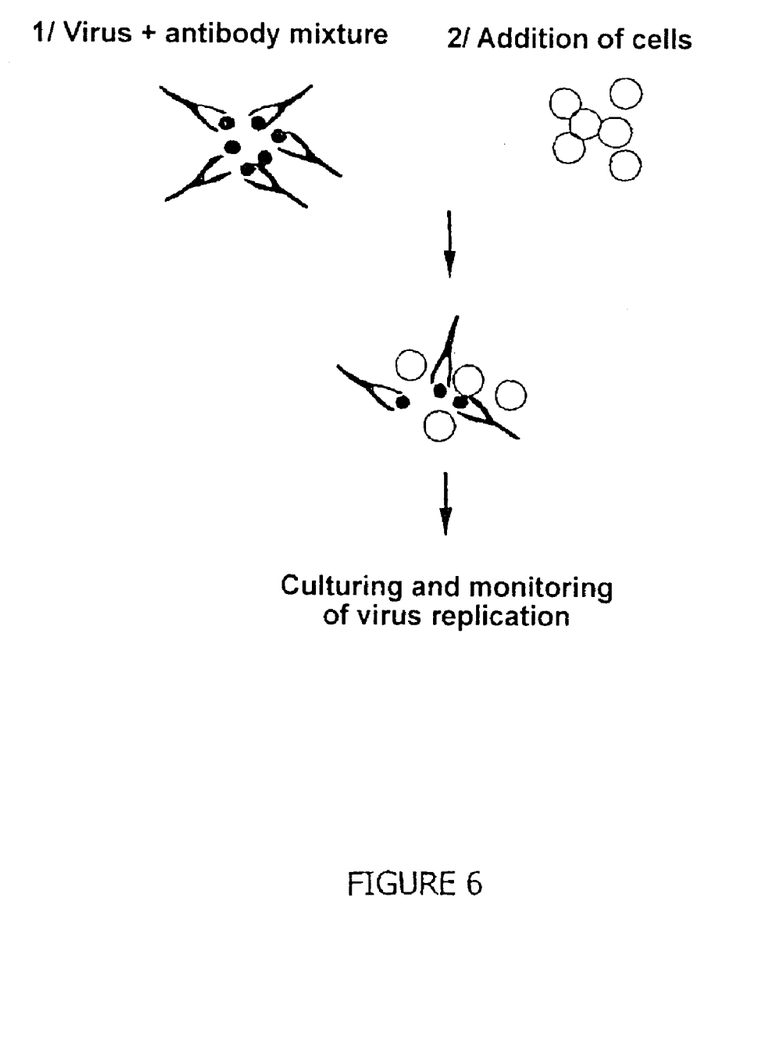
FIG. 6 is a diagram summarizing the virus neutralization protocol.

3.1. Experimental Protocol:

50 μL of IgG$_3$ solution+50 μL of diluted virus (in 10% RPMI medium) are incubated for 1 hour at 37° C. in a 96-well plate. Then, 0.3×10$^6$ cells per well are added to the mixture and placed at 37° C. for 1 hour. Following two washes with 0% RPMI medium, the cells are placed in a 24-well plate in 10% RPMI medium in the presence of IgG$_3$s (FIG. 6).

3.2. Results (cf. Table 5)

TABLE 5

Neutralization of NDK/PBL (29 Feb. 1996) by IgG$_3$s or IgG$_{1,2,4}$s of ARG CH, ETC MA, AUR PH and THO MI.

| | Dose (μg/mL) | Day 3 | Day 4 | Day 5 | Day 6 |
|---|---|---|---|---|---|
| ARG CH IgG$_3$ | 40 μg/mL | − | (+) | ++ | ++T |
| | | − | (+) | ++ | ++T |
| | 20 μg/mL | − | − | (+) | + |
| | | − | − | + | ++T |
| | 10 μg/mL | (+) | + | ++ | ++T |
| | | (+) | + | ++ | ++T |
| | 5 μg/mL | − | − | (+) | + |
| | | (+) | (+) | ++ | ++T |
| ARG CH IgG$_{1,2,4}$ | 40 μg/mL | − | (+) | + | ++T |
| | | − | (+) | ++ | ++T |
| | 20 μg/mL | (+) | + | ++ | ++T |
| | | − | (+) | ++ | ++T |
| ETC MA IgG$_3$ (13 Sep. 2001) | 10 μg/mL | + | ++ | ++ | ++T |
| | | − | (+) | + | ++T |
| | 5 μg/mL | (+) | + | ++ | ++T |
| | | (+) | + | ++ | ++T |
| | 100 μg/mL | (+) | + | ++ | ++T |
| | | − | (+) | ++ | ++T |
| | 50 μg/mL | (+) | + | ++ | ++T |
| | | − | (+) | ++ | ++T |
| | 25 μg/mL | (+) | ++ | + | ++T |
| | | (+) | + | ++ | ++T |
| | 12.5 μg/mL | − | − | ++ | ++T |
| | | (+) | (+) | ++ | ++T |
| ETC MA IgG$_{1,2,4}$ (13 Sep. 2001) | 100 μg/mL | (+) | ++ | ++ | ++T |
| | | (+) | + | ++ | ++T |
| | 50 μg/mL | (+) | ++ | ++ | ++T |
| | | (+) | + | + | ++T |
| | 25 μg/mL | (+) | (+) | ++ | ++T |
| | | − | − | ++ | ++T |
| | 12.5 μg/mL | (+) | ++ | ++T | ++T |
| | | − | (+) | ++ | ++T |
| Positive control serum for the neutralization | 1/50 | − | − | − | − |
| | 1/100 | − | − | − | − |
| | | − | − | − | − |
| CONTROL MT4 cells | | − | − | − | − |
| | | − | − | − | − |
| VIRUS NDK/PBL (29 Feb. 1996) | 10$^{-4}$ | (+) | + | ++ | ++T |
| | | (+) | + | ++ | ++T |

−: absence of syncitia
+: presence of syncitia

The IgG$_3$S isolated from two patients neutralize HIV as shown in Table 5. With 40 μg and 20 μg of IgG$_3$, a neutralization of the virus is observed, that is to say an absence of syncitia, whereas the IgG$_{1,2,4}$s are limited to the dose of 40 μg/mL.

Example 4

Virolysis of HIV by the Complement and Total IgG$_3$s, Purified from Non-Progressor HIV-Positive Patients

4.1. Experimental Protocol:

10 or 20 μg of IgG3+12.5 μL of pure virus are incubated for 1 hour at 4° C. with rotary stirring. Then, 1 mL of rabbit complement at 1/12 (dilution of the complement in 10% RPMI medium heated to 37° C.) is added to the mixture, and the whole is incubated for 30 minutes at 37° C. The samples are diluted and P24 is determined (COULTER kit 6604535).

4.2. Results: (Table 6)

TABLE 6

Test for lysis by the complement (virus NDK/PBL of 29 Feb. 1996)

| Sample | % lysis |
|---|---|
| 20 μg ARG CH IgG3 + 12.5 μL virus + 1 mL complement at 1/12 | 57.60% |
| 10 μg ARG CH IgG3 + 12.5 μL virus + 1 mL complement at 1/12 | 60.30% |
| 12.5 μL virus + 1 mL 10% RPMI, no triton | 18.60% |
| 12.5 μL virus + 1 mL complement at 1/12 | 1.70% |
| 12.5 μL virus + 1 mL 10% RPMI + triton | 100% |

The complement binds to the IgG$_3$-virus complex and lyses the virus, as shown in Table 6 where 60% of the virus is lysed in the presence of 10 μg of IgG$_3$.

The neutralization of viruses and virolysis in the presence of complement give IgG$_3$s great potential for use as therapeutic antibodies in HIV infection or in any other viral infection in which IgG$_3$s will be present either in the conventional manner or in the form of the variant.

This study suggests that the complement in addition with the anti-R7V antibodies in the blood of people infected with HIV can lyse the virus and destroy its infectiousness.

The presence of infectious viruses in the plasma is 10 to 100 times greater in progressors than in non-progressors. This is because, since the progressor patients have no anti-R7V antibodies and hence no anti-R7V IgG$_3$s, there will be no neutralization or virolysis and thus presence of viruses.

In conclusion, the inventors have shown that the antibodies for therapeutic use of IgG$_3$ type which bind the complement and ensure virolysis will be very effective not only in precipitating and neutralizing the virus but also in destroying it.

BIBLIOGRAPHIC REFERENCES

Coligan et al., Current Protocols in Immunology [updated annually] (4 volumes), published by the "National Institutes of Health" by Wiley Interscience.

Harlow et al., (1988) Antibodies: A Laboratory Manual, Cold Spring Harbor Publications, pp. 726.

Köhler and Milstein (1975) Nature, 256: 495-497.

Sambrook, J., Frischt, E. F. and Maniatis, T., Molecular cloning. A Laboratory Manual. Cold Spring Harbor Laboratory Press, Cold Spring Harbor, N.Y., 1989.

The invention claimed is:

1. A purified and/or isolated human immunoglobulin of class IgG3, which selectively binds the R7V epitope of the gp160 protein of the HIV-1 virus, said epitope comprising the sequence of SEQ ID NO: 1, having the following characteristics:

(i) a patient serum halflife of at least one month;

(ii) a heavy chain having a molecular weight of about 50 kDa, as determined by SDS-PAGE; and (iii) comprising the complement binding site of normal IgG3s.

2. An immunoglobulin according to claim 1, isolated and/or purified from a non-progressor HIV seropositive patient.

3. A composition comprising an immunoglobulin according to claim 1, and a pharmaceutically acceptable carrier, diluent or excipient.

4. A human immunoglobulin variant of class IgG3, which:

(i) selectively binds the R7V epitope of the gp160 protein of the HIV-1 virus, said epitope comprising the sequence of SEQ ID NO: 1;

(ii) is purified and/or isolated from a patient infected with human immunodeficiency virus, wherein said patient is a non-progressor;

(iii) has a patient serum halflife of at least one month;

(iv) has a heavy chain with a molecular weight of about 50 kDa, as determined by SDS-PAGE; and (v) comprises the complement binding site of normal IgG3s.

5. A method of purifying and/or isolating a human immunoglobulin variant of class Ig3, which selectively binds the R7V epitope of the gp160 protein of the HIV-1 virus, said epitope comprising the sequence of SEQ ID NO: 1 wherein said IgG3 variant has a patient serum half-life of at least one month and has a heavy chain of about 50 kDa, as determined by SDS-PAGE; said method comprising:

(i) identifying one or more non-progressor patients infected with human iminunodeficiency virus and obtaining a serum sample from said patient(s);

(ii) purifying and/or isolating IgG3s from said serum sample;

(iii) determining the molecular weight of the heavy chain of said purified and/or isolated TgG3s.

6. A method in accordance with claim 5, further comprising obtaining multiple serum samples from said patient over time, and determining the presence of IgG3 for at least a period of one-month.

* * * * *

UNITED STATES PATENT AND TRADEMARK OFFICE
CERTIFICATE OF CORRECTION

PATENT NO. : 7,306,798 B2  Page 1 of 1
APPLICATION NO. : 10/504802
DATED : December 11, 2007
INVENTOR(S) : Jean-Claude Chermann, Camille Haslin and Ricardo De Oliveira It is certified that error appears in the above-identified patent and that said Letters Patent is hereby corrected as shown below:

Column 17, line 64, "halflife" should read --half-life--.
Column 18, line 8, after "claim 1" delete --,--.
Column 18, line 18, "halflife" should read --half-life--.
Column 18, line 27, after "SEQ ID NO: 1" insert --,--.
Column 18, line 61, "TgG3s" should read --IgG3s--.

Signed and Sealed this

Twenty Second Day of April, 2008

JON W. DUDAS
*Director of the United States Patent and Trademark Office*